United States Patent
Kumagai

(10) Patent No.: US 11,735,313 B2
(45) Date of Patent: Aug. 22, 2023

(54) INFORMATION PROCESSING DEVICE, METHOD OF GENERATING INFORMATION, INFORMATION PROCESSING SYSTEM, AND NON-TRANSITORY RECORDING MEDIUM

(71) Applicant: Shohgo Kumagai, Kanagawa (JP)

(72) Inventor: Shohgo Kumagai, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 158 days.

(21) Appl. No.: 17/172,303

(22) Filed: Feb. 10, 2021

(65) Prior Publication Data

US 2021/0256289 A1    Aug. 19, 2021

(30) Foreign Application Priority Data

Feb. 18, 2020  (JP) .................................. 2020-025516

(51) Int. Cl.
| | | |
|---|---|---|
| *G16H 30/40* | (2018.01) | |
| *G06T 7/00* | (2017.01) | |
| *G06V 10/75* | (2022.01) | |
| *G06V 10/74* | (2022.01) | |
| *G06V 10/40* | (2022.01) | |

(52) U.S. Cl.
CPC ........... *G16H 30/40* (2018.01); *G06T 7/0014* (2013.01); *G06V 10/40* (2022.01); *G06V 10/751* (2022.01); *G06V 10/761* (2022.01)

(58) Field of Classification Search
None
See application file for complete search history.

(56) References Cited

U.S. PATENT DOCUMENTS

| | | | |
|---|---|---|---|
| 9,424,268 B2 * | 8/2016 | Barnett | G06F 16/1748 |
| 10,803,586 B1 * | 10/2020 | Reunanen | G06T 7/0014 |
| 2011/0007968 A1 * | 1/2011 | Yamada | H04N 17/00 382/165 |
| 2011/0292219 A1 * | 12/2011 | Chang | G06T 7/80 348/181 |
| 2014/0050369 A1 * | 2/2014 | Ghuge | H04N 23/631 382/224 |
| 2017/0186144 A1 * | 6/2017 | Chien | G06T 5/002 |
| 2018/0365479 A1 * | 12/2018 | Lee | G06V 40/1335 |
| 2019/0001664 A1 * | 1/2019 | Yamazaki | B41J 11/0095 |
| 2019/0012809 A1 * | 1/2019 | Li | G06F 3/011 |
| 2019/0066492 A1 * | 2/2019 | Nijhuis | G08G 1/054 |
| 2019/0287241 A1 * | 9/2019 | Hill | A61B 6/5282 |
| 2019/0388182 A1 * | 12/2019 | Kumar | G06T 7/0016 |

(Continued)

FOREIGN PATENT DOCUMENTS

| | | |
|---|---|---|
| JP | 2005-222323 | 8/2005 |
| JP | 2007-090077 | 4/2007 |

(Continued)

*Primary Examiner* — Michelle M Entezari
(74) *Attorney, Agent, or Firm* — IPUSA, PLLC

(57) ABSTRACT

An information processing device includes circuitry. The circuitry calculates a matching degree between two images of an image pair. The matching degree of the image pair is one of a plurality of matching degrees of a plurality of image pairs. The circuitry generates information on sameness between two image groups of an image group pair based on the plurality of matching degrees of the plurality of image pairs. The image group pair includes the plurality of image pairs.

8 Claims, 14 Drawing Sheets

(56) References Cited

U.S. PATENT DOCUMENTS

| | | | |
|---|---|---|---|
| 2020/0150275 A1* | 5/2020 | Zhu | G06T 19/20 |
| 2021/0049128 A1* | 2/2021 | Kernick | G06V 40/161 |
| 2021/0118213 A1* | 4/2021 | Ji | G06T 7/596 |
| 2022/0020136 A1* | 1/2022 | Hyatt | G06T 7/001 |

FOREIGN PATENT DOCUMENTS

| | | |
|---|---|---|
| JP | 2007-159934 | 6/2007 |
| WO | WO-2020197495 A1 * | 10/2020 |

* cited by examiner

X: DIFFERENCE

| IMAGE NAME OF IMAGE GROUP A | IMAGE NAME OF IMAGE GROUP B | MATCHING DEGREE OF IMAGE PAIR |
|---|---|---|
| ImageA1 | ImageB1 | 0.96 |
| ImageA2 | ImageB2 | 1.0 |
| ImageA3 | ImageB3 | 0.97 |
| ImageA4 | ImageB4 | 0.93 |
| ImageA5 | ImageB5 | 0.94 |

FIG. 17

| MATCHING DEGREE | 0.95 |
|---|---|
| RESULT | MATCH |

| No. ▼ | IMAGE GROUP A | IMAGE GROUP B | MATCHING DEGREE ▼ |
|---|---|---|---|
| 1 | △ ○ □ | △ ○ □ | 0.97 |
| 2 | △ | △ | 1.0 |
| 3 | ABC | ABC | 0.88 |

FIG. 18

| MATCHING DEGREE: COLOR | 0.88 |
|---|---|
| MATCHING DEGREE: SHAPE | 0.86 |
| MATCHING DEGREE | 0.87 |
| RESULT | NOT MATCH |

| No. ▼ | IMAGE GROUP A | IMAGE GROUP B | MATCHING DEGREE: COLOR ▼ | MATCHING DEGREE: SHAPE ▼ |
|---|---|---|---|---|
| 1 | △ ○ □ | △ ○ □ | 0.99 | 0.95 |
| 2 | △ | △ | 0.71 | 0.81 |
| 3 | ABC | ABC | 0.94 | 0.82 |

INFORMATION PROCESSING DEVICE, METHOD OF GENERATING INFORMATION, INFORMATION PROCESSING SYSTEM, AND NON-TRANSITORY RECORDING MEDIUM

CROSS-REFERENCE TO RELATED APPLICATION

This patent application is based on and claims priority pursuant to 35 U.S.C. § 119(a) to Japanese Patent Application No. 2020-025516, filed on Feb. 18, 2020, in the Japan Patent Office, the entire disclosure of which is hereby incorporated by reference herein.

BACKGROUND

Technical Field

Embodiments of the present disclosure relate to an information processing device, an information processing system, a method of generating information, and a non-transitory recording medium storing instructions for executing a method of generating information.

Related Art

With respect to systems that output images, there is a situation in which whether an output of one system and another output of another system are exactly the same or not, namely "match exactly" or not, is desired to be determined. In addition, there is a situation in which whether the output of the one system and the other output of the other system" are determined to be the same by the human visual perception" or not is desired to be determined.

For example, a technique for comparing between computed tomography (CT) images obtained by CT screening has been devised. In such a technique, severity deviation data is determined based on data of two anatomical images for a purpose of diagnosing severity of a disease.

SUMMARY

An exemplary embodiment of the present disclosure includes an information processing device including circuitry. The circuitry calculates a matching degree between two images of an image pair. The matching degree of the image pair is one of a plurality of matching degrees of a plurality of image pairs. The circuitry generates information on sameness between two image groups of an image group pair based on the plurality of matching degrees of the plurality of image pairs. The image group pair includes the plurality of image pairs.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 17 is a diagram illustrating an example of a list screen when a user inputs "MATCH", according to one or more embodiments; and FIG. 18 is a diagram illustrating an example of a list screen displaying a list of image pairs displayed by a terminal device based on features of color and shape, according one or more embodiments.

Figure 1:
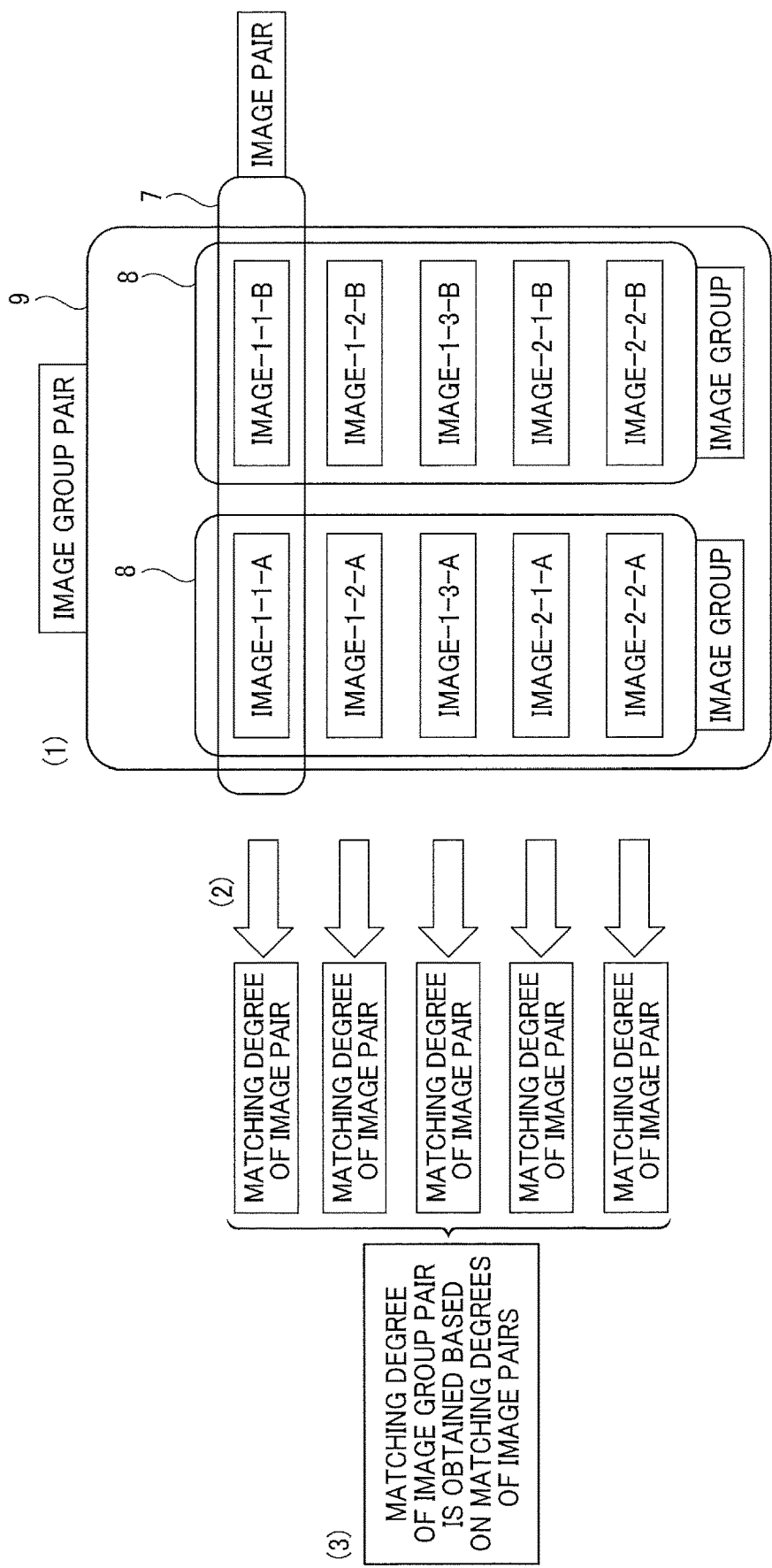
FIG. 1 is a schematic diagram illustrating operation performed by an information processing system according to one or more embodiments.

The accompanying drawings are intended to depict example embodiments of the present disclosure and should not be interpreted to limit the scope thereof. The accompanying drawings are not to be considered as drawn to scale unless explicitly noted.

DETAILED DESCRIPTION

The terminology used herein is for describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof. In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operation in a similar manner, and achieve a similar result.

A description is given below of an information processing device and a method of generating information performed by the information processing device according to one or more of the embodiments of the present disclosure, with reference to the drawings.

Overview of Operation

First, a description is given below of an example of a situation in which two image groups of an image group pair are desired to be compared with each other. That is, the image group pair is a pair of the two image groups for comparison. For example, when a printer driver or a drawing module is newly developed, a person in charge of the manufacturer checks whether there is no failure, or problem, with the new printer driver or the new drawing module. As such a method of checking, there is a method in which the same evaluation file is used to print two images, for example. One of the two printed image is printed by an old printer driver or an old drawing module, of which operation has been already checked and confirmed, and the other one of the two printed image is printed by a new printer driver or a new drawing module, which is a target to be checked. When an information processing system compares the two printed images and determines that the two printed images are completely identical to each other (match exactly), or when the two printed images are determined as the same by human visual perception, the new printer driver or the new drawing module is determined as being ready for launch, or release. On the other hand, the two printed images are determined as being different from each other, this means that there is a problem with the new printer driver or the new drawing module, and improvement on the new printer driver or the new drawing module is required.

However, a result obtained by comparing two images with each other varies depending on the evaluation file to be printed. Accordingly, there is a demand to use a large number of image pairs for comparison and obtain a determination result as a whole, OK (no problem) or NG (suspected to have a problem).

In consideration of the above-described demand, according to one of the embodiments of the disclosure, a matching degree of an image group pair is calculated based on a plurality of matching degrees of a plurality of image pairs, as illustrated in FIG. 1. The matching degree of an image group pair is a degree of matching between two image groups included in the image group pair for comparison. A matching degree of an image pair is a degree of matching between the two images included in the image pair for comparison. In addition, terms of "degree of matching" is replaceable with terms of "matching degree" in the description of the present embodiment given below. The matching degree indicates how much two targets for comparison are identical to each other in the following description of the present embodiment of the disclosure.

FIG. 1 is a schematic diagram illustrating operation performed by an information processing system according to the present embodiment. In the information processing system, N image data items (images to be printed, which is described later) are generated from one evaluation file, for example. For example, when the evaluation file has ten pages, the number of image data items is ten (N=10). That is, one or more image data items are generated from the one evaluation file. When a plurality of evaluation files is used, a total number of pages of the plurality of evaluation files is equal to N.

The old printer driver or the old drawing module (hereinafter referred to as an old system) of which the operation has been already checked, or confirmed, generates N image data items. In addition, the new printer driver or the new drawing module (hereinafter referred to as a new system) generates N image data items. In the example of FIG. 1, five image data items are generated by each of the old system and the new system.

(1)

A pair of image data items (a pair of images) is referred to as an "image pair 7", in the description of the present embodiment. The image pair 7 includes a data item (an image) generated based on an evaluation file by the old system and another data item (another image) generated based on the same evaluation file by the new system. The image pair 7 is a pair of the two images for comparison. There is a plurality of image pairs 7. In addition, the images (a group of images) generated by each of the old system and the new system based on the evaluation file (one or more evaluation files) is referred to as an "image group 8", in the description of the present embodiment. There are two image groups 8 for comparison. In addition, the two image groups 8 are a pair of image groups for comparison, which is referred to as an "image group pair 9", in the description of the present embodiment.

(2)

The information processing system calculates, computes, or obtains, a degree of matching between the two images of each image pair 7. Hereinafter, the degree of matching of an image pair may be referred to as a degree of image pair matching, a matching degree of an image pair, or an image pair matching degree, in the description of the present embodiment of the disclosure. The same applies to a degree of matching of an image group pair. Accordingly, for each image pair 7 included in the image group pair 9, a matching degree is obtained. The matching degree may be calculated, computed, or obtained based on a pixel unit or by using a basis close to the human visual perception.

(3)

The information processing system calculates a matching degree of the image group pair 9 based on a plurality of matching degrees of the plurality of image pairs 7. For example, the information processing system calculates, an arithmetic mean, a geometric mean, a weighted mean, a harmonic mean, a trimmed mean, a sample variance, an unbiased variance, or the like of the plurality of matching degrees of the plurality of image pairs 7. The information processing system determines that two image groups included in the image group pair 9 are identical to each other, namely match, or are the same with each other, when the matching degree of the image group pair 9 is equal to or greater than a threshold value.

As described above, the information processing system according to the present embodiment of the disclosure calculates the matching degree of the image group pair 9 based on the plurality of matching degrees of the plurality of image pairs 7, thereby determining whether the two image groups 8 are identical to each other (match), as a whole based on comparison results obtained from a large number of image pairs, which are the image pairs 7.

Regarding Terms

"Matching degree" or "degree of matching" is information indicating how much two images match, namely how much the two images are identical to each other. "Matching degree" or "degree of matching" may be referred to as, or replaceable with "similarity degree" or "degree of similarity" in the description of the present embodiment.

Information on sameness between two image groups of an image group pair (may be simply referred to as information on sameness of an image group pair) is information indicating how much the two image groups included in the image group pair are identical to each other. In the description of the present embodiment of the disclosure, the information on sameness may be referred to as, or replaceable with matching information. In the present embodiment described below, as an example, the information on the sameness includes information indicating whether the two image groups are regarded as the same or not ("MATCH" or "NOT MATCH"), and information on a matching degree of the image group pair.

Example Configuration

Figure 2:
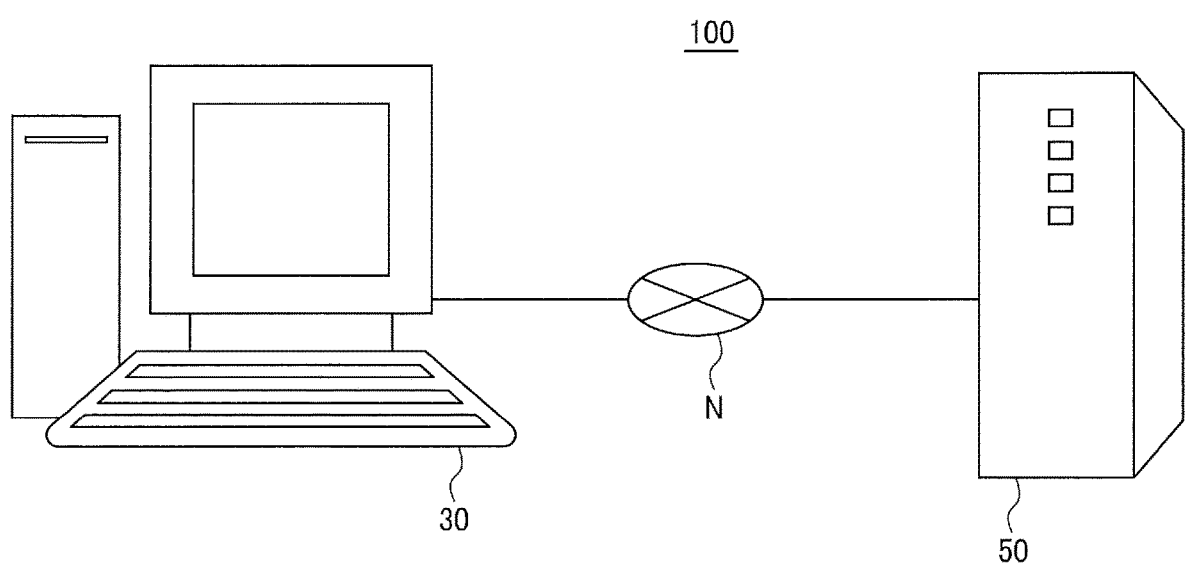
FIG. 2 is a schematic diagram illustrating an example of a configuration of an information processing system that performs a matching determination with respect to an image group pair according to one or more embodiments.

FIG. 2 is a schematic diagram illustrating an example of a configuration of an information processing system 100 that determines whether two image groups included in an image group pair are identical to each other or not, namely determines sameness between the two image groups of the image group pair, according the present embodiment of the disclosure. Hereinafter, the determination may be referred to as a matching determination or a sameness determination in the description of the present embodiment. In a system configuration according to the present embodiment, the information processing device 50 corresponding to a server of a client-server type performs the matching determination with respect to the image group pair. However, the terminal device 30 alone may perform the matching determination.

In the information processing system 100, the terminal device 30 and the information processing device 50 are capable of communicating with each other through a network N. The information processing device 50, which is also called as a server or a server device, is a device that mainly performs information processing via a network. In addition, the information processing device 50 is a device that responds to a request received through the network with information or a processing result.

The information processing device 50 may be on the Internet or on-premises. With any configuration, the information processing system 100 may be referred to as a cloud system. The cloud system is a system in which resources on a network are available without a specific hardware resource.

The information processing device 50 is used as a so-called web server that generates screen information of a portal screen to receive operations and provides the screen information to the terminal device 30. The screen information is described with, such as for example, hypertext markup language (HTML), extensible markup language (XML), script language, or cascading style sheet (CSS), and is mainly analyzed and displayed by browser software. The terminal device 30 on which a web browser is operating receives the screen information and displays a web page, accordingly. The web page includes a user interface that receives settings for the matching determination with respect to the image group pair, and a screen that displays the information on the sameness between the two image groups of the image group pair. The user specifies one or more of an operating system (OS), a printer driver, a page description language (PDL) module, an evaluation file, and the like, and requests the information processing device 50 to perform processing of the matching determination.

The web page may be provided by a web application. "Web application" is defined as software or a mechanism of software that is implemented by cooperation between a program executed on a browser and written in a programming language such as JavaScript (registered trademark) and a program provided by a web server. The web page may be dynamically changed by the web application.

On the other hand, the terminal device 30 receives the screen information from the information processing device 50 and displays the screen information on a web browser to receive user operations including the operations for settings related to the matching determination with respect to the image group pair including the two image groups for comparison. The web browser operating on the terminal device 30 transmits the settings related to the matching determination to the information processing device 50 to request to perform the processing of the matching determination.

The terminal device 30 may be any device on which software such as a web browser is operable. Examples of the terminal device 30 include a personal computer (PC), a tablet terminal, a personal digital assistant (PDA), and a smartphone. In addition, an electronic whiteboard, a video conference terminal, or the like may be used as the terminal device 30. In alternative to the web browser, application software dedicated to the information processing system 100 may be operated on the terminal device 30. A comparison result (information on the sameness between two image groups of the image group pair) obtained by the matching determination may be displayable on the terminal device 30. In addition, the comparison result may be transmitted by the information processing device 50 via e-mail or may be stored on the network.

Example of Hardware Configuration

Figure 3:
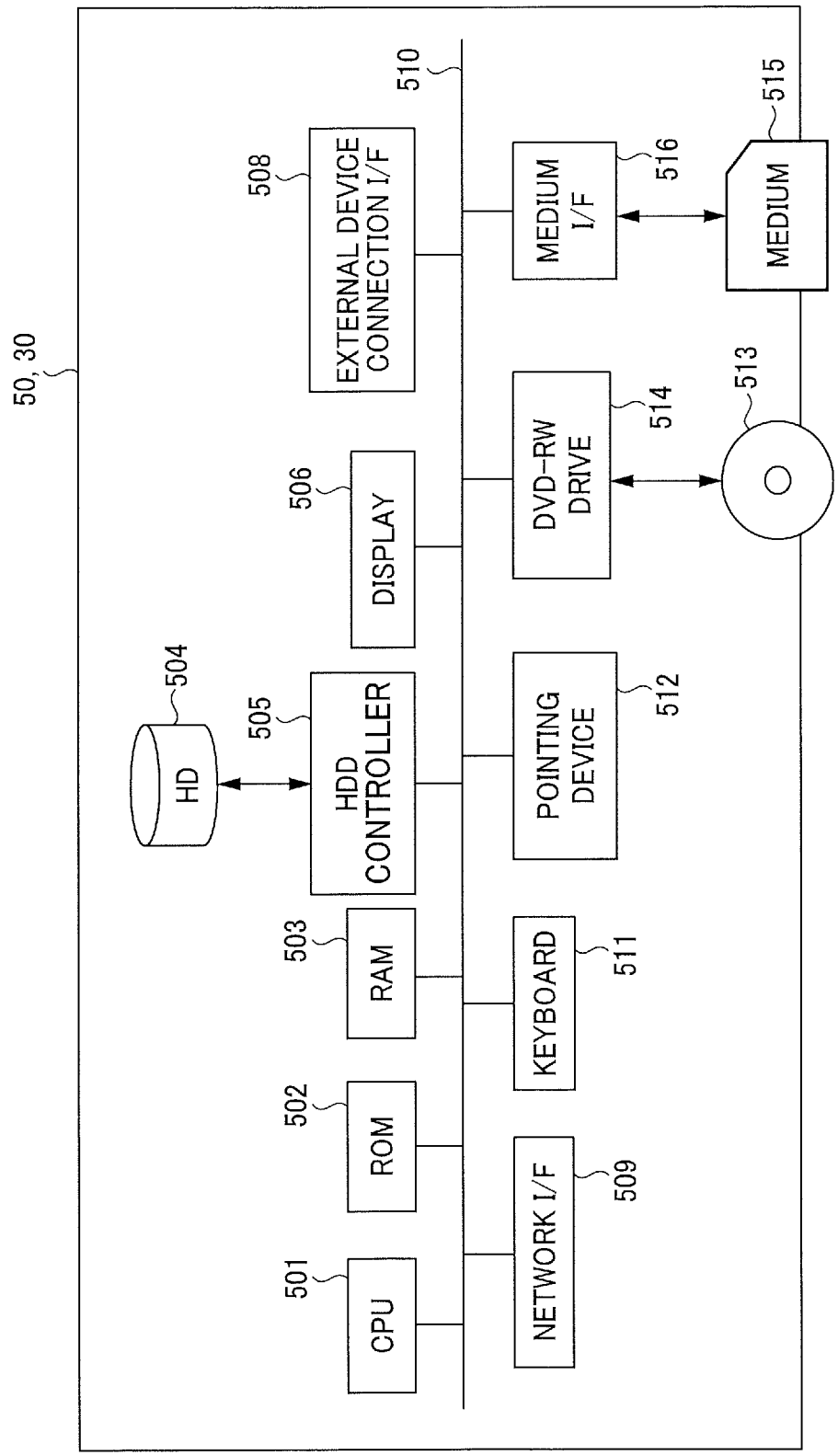
FIG. 3 is a block diagram illustrating a hardware configuration of a terminal device or an information processing device according to one or more embodiments.

FIG. 3 is a block diagram illustrating a hardware configuration of each of the terminal device 30 and the information processing device 50 according to the present embodiment of the disclosure. In the following description of the hardware configuration given below, the information processing device 50 is used as an example to describe the hardware configuration.

As illustrated in FIG. 3, the information processing device 50 is implemented by a computer and includes a central processing unit (CPU) 501, a read only memory (ROM) 502, a random access memory (RAM) 503, a hard disk (HD) 504, a hard disk drive (HDD) controller 505, a display 506, an external device connection interface (I/F) 508, a network IF 509, a bus line 510, a keyboard 511, a pointing device 512, a digital versatile disk-rewritable (DVD-RW) drive 514, and a medium IF 516.

The CPU 501 controls the entire operation of the information processing device 50. The ROM 502 stores a program such as an initial program loader (IPL) used for driving the CPU 501. The RAM 503 is used as a work area for the CPU 501. The HD 504 stores various data such as a program. The HDD controller 505 controls reading and writing of various data from and to the HD 504 under control of the CPU 501. The display 506 displays various information such as a cursor, a menu, a window, a character, or an image. The external device connection I/F 508 is an interface for connecting to various external devices. Examples of the external devices include, but are not limited to, a universal serial bus (USB) memory and a printer. The network I/F 509 is an interface for performing data communication using a communication network. The bus line 510 is an address bus, a data bus, or the like for electrically connecting the components such as the CPU 501 illustrated in FIG. 3 each other.

The keyboard 511 is an example of an input device provided with a plurality of keys for allowing a user to input characters, numerals, or various instructions. The pointing device 512 is an example of an input device that allows a user to select or execute a specific instruction, select a target for processing, or move a cursor being displayed. The DVD-RW drive 514 reads and writes various data from and to a DVD-RW 513, which is an example of a removable storage medium. The removable storage medium is not limited to the DVD-RW and may be a digital versatile disc-recordable (DVD-R) or the like. The medium/F 516 controls reading and writing (storing) of data from and to the storage medium 515 such as a flash memory.

Functions

Figure 4:
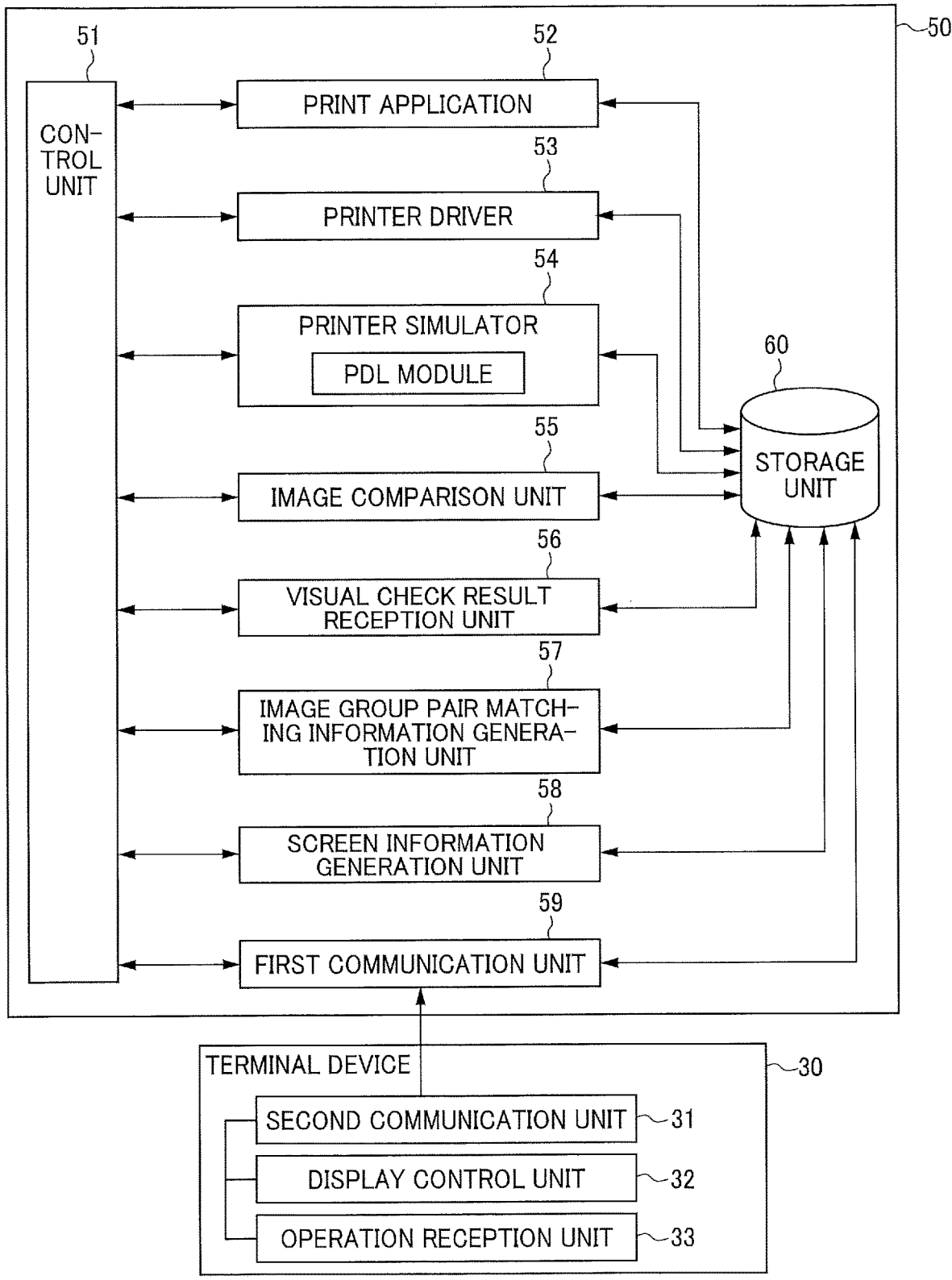
FIG. 4 is a block diagram illustrating an example of a functional configuration of an information processing device and a terminal device according to one or more embodiments.

FIG. 4 is a block diagram illustrating an example of a functional configuration of the information processing device 50 and the terminal device 30 according to the present embodiment of the disclosure.

Information Processing Device

The information processing device 50 includes a control unit 51, a print application 52, a printer driver 53, a printer simulator 54, an image comparison unit 55, a visual check result reception unit 56, an image group pair matching information generation unit 57, a screen information generation unit 58, and a first communication unit 59. Each functional unit included in the information processing device 50 is implemented by operating any of components illustrated in FIG. 3 according to an instruction from the CPU 501 according to a program expanded from the HD 504 to the RAM 503.

The first communication unit 59 communicates with the terminal device 30 to transmit or receive various information. For example, the first communication unit 59 receives from the terminal device 30 the settings related to the matching determination and transmits to the terminal device 30 the information on the sameness of an image group pair.

The control unit 51 controls the entire processing related to the matching determination. For example, the control unit 51 manages a flow of the processing based on the settings related to the matching determination received from a user and invokes necessary functions under the print application 52. A control tool such as Jenkins is known as the control unit 51. In addition, Robotic Process Automation (RPA) may be used. The RPA is a concept in which a software-type robot in a personal computer substitutes and automates desk works (mainly routine works).

The print application 52 is application software that runs on the OS installed on the information processing device 50. That is, the print application 52 is an application that is capable of, at least, opening an evaluation file and that invokes the printer driver 53 to start printing. The print application 52 may be any types of software that invokes the printer driver 53. Examples of the software includes word processing software, web browser software, illustration software, paint software, and the like. In addition, the number of print applications 52 may be two or more. In a case of a plurality of print applications 52, the information processing device 50 performs the matching determination with respect to the image group pair 9 using different evaluation files.

The printer driver 53 is software that runs on the OS installed on the information processing device 50. The printer driver 53 is inherently software that acts as an intermediary between a computer and an image forming apparatus to allows a user to easily use the image forming apparatus. The printer driver 53 has a function of displaying a user interface screen that receives print settings (also referred to as print conditions) and a function of generating print data described in a PDL. The PDL includes, for example, PostScript (registered trademark) and Printer Control Language (PCL). In addition to the above-mentioned types, there are various other types, which depend on a manufacturer of the image forming apparatus. In the image forming apparatus, a PDL module corresponding to each PDL is operating.

The printer simulator 54 is software that runs on the OS installed on the information processing device 50. The printer simulator 54 performs, on the information processing device 50, rendering executed by the image forming apparatus. The rendering may be referred to as a Raster Image Processer (RIP) or drawing processing. In addition, software that performs the rendering may be referred to as a PDL module or a drawing processing unit. The printer simulator 54 has one or more PDL modules. The printer simulator 54 may be on a network that is accessible by the information processing device 50 in alternative to or in addition to being included in the information processing device 50.

The PDL module performs color matching processing and screening processing to generate an image to be printed for each of the colors, Cyan (C), Mugenda (M), Yellow (Y), and Key plate (K), which are used by the image forming apparatus for printing. The color matching processing is a process of converting, at an optimum conversion ratio, input color (or monochrome) print data into data for printing with four toners each of which corresponds to one of the colors, C, M, Y, and K of the image forming apparatus. Print data input from the print application 52 may be represented by an RGB color space or a CMYK color space, but, in general, the RGB color space is used in the print application 52. The printer simulator 54 converts the print data from the RGB color space into a device independent color space by color matching processing, and then converts into a device color space that is suitable for characteristics of the image forming apparatus, so that the print data is converted into the CMYK color space. A known conversion formula may be used as a conversion formula for converting from RGB to C, M, Y, K, or a conversion formula optimized for the image forming apparatus may be used.

The screening processing is a pseudo gradation expression method such as a dither method. The screening processing is processing for changing a size or density of halftone dots to express a difference in shading by using an optical illusion and converts bitmap data into an image (image to be printed) that is able to be printed by the image forming apparatus. In the image to be printed, 1 (ON: draw) or 0 (OFF: not draw) is set for each dot corresponding to a pixel drawn as a point by laser or ink.

The image comparison unit 55 compares two target images to be printed to calculate the matching degree (The image comparison unit 55 compares the two images). The matching degree may be a single numerical value or may be a set of a plurality of matching degrees each of which is obtained by focusing on a certain feature. In addition to the matching degree that is obtained based on whether the two images exactly match each other in a pixel unit, the matching degree of which a value indicates the two images are determinable as the same by human visual perception may be obtained.

Examples of a feature in an image, namely examples of an image feature, (features to be focused on when calculating the matching degree of the image pair 7) include a feature of color, shape, layout, hue, saturation, lightness, luminance, contrast, color histogram, edge, corner, character thickness, font, dither, character-likeness, illustration-likeness, graphic-likeness, photographic-likeness, error diffusion, occlusion, target or background, modulation transfer function (MTF) (blurring), signal/noise (S/N) (noise), etc.

Color: A color of a color system, such as an XYZ color system, which does not depend on a device. For example, the image comparison unit 55 extracts several colors from each of the images for comparison and compares between the images with respect to the numbers of pixels of the same colors to calculate the matching degree.

Shape: A figure such as a circle or square included in an image. For example, the image comparison unit 55 extracts a set of continuous edges that are equal to or greater than a certain length from each of the images for comparison and compares between the images with respect to the edges at the same position (for example, compares the lengths) to calculate the matching degree.

Layout: An arrangement of one or more characters, one or more figures, one or more photographs, or the like. For example, the image comparison unit 55 detects characters, figures, photographs, or the like, from each of the images for comparison and compares between the images in a manner that the characters, the figures, or the photographs are compared with each other (for example, how each comparison targets are overlapped with each other is checked) to calculate the matching degree.

Hue: A color aspect such as red, orange, yellow, green, blue, or purple. For example, the image comparison unit 55 extracts specific colors from each of the images for comparison and compares between the images with respect to the numbers of pixels of the same colors to calculate the matching degree.

Saturation: Brightness of color (chromatic intensity). The image comparison unit 55 calculates the saturation of each of the two images for comparison and compares between the two images with respect to the saturation to calculate the matching degree.

Lightness: Lightness of color. The image comparison unit 55 calculates the lightness of each of the two images for comparison and compares between the two images with respect to the lightness to calculate the matching degree.

Luminance: A YUV value converted from RGB. The image comparison unit 55 calculates the luminance of each of the two images for comparison and compares between the two images with respect to calculate the matching degree.

Contrast: The difference in brightness between a light part and a dark part (contrast ratio). The image comparison unit 55 calculates the contrast of each of the two images for comparison and compares between the two images with respect to the contrast to calculate the matching degree.

Color histogram: A histogram of each color. The image comparison unit 55 calculates the color histogram of each of the images for comparison by reducing the number of distinct colors equal to or less than a certain level and compares between the images with respect to the histograms to calculate the matching degree.

Edge: The strength or density of an edge included in an image. For example, the image comparison unit 55 calculates the density of an edge having the strength equal to or greater than a certain level for each of the two images for comparison and compares between the two images with respect to the edge density to calculate the matching degree.

Corner: A vertex formed by two straight lines. For example, the image comparison unit 55 detects a corner from each of the two images for comparison, compares between the corners at positions corresponding to each other (for example, compares between the corners of the images with respect to the length, the angle, etc.) to calculate the matching degree.

Character thickness: The thickness of the lines of a character. The image comparison unit 55 detects a character from each of the images for comparison and compares between the characters with respect to a length of continuous black pixels in the longitudinal direction and the perpendicular direction to calculate the matching degree.

Font: The shape of a font. The image comparison unit 55 superimposes the same characters on each other to calculates the matching degree.

Dither: The number of gradations of color. The image comparison unit 55 specifies a color from a certain range of dots and compares between the images with respect to the color at the same position to calculate the matching degree.

Character-likeness, illustration-likeness, figure-likeness, and photographic-likeness: The plausibility of a character, the plausibility of an illustration, the plausibility of a figure, and the plausibility of a photograph, respectively, each of which is calculated by a predetermined method. The image comparison unit 55 calculates, as the matching degree, a degree of matching with respect to the plausibility of character-likeness, for example.

Error diffusion: An index of how a neutral color is expressed. The image comparison unit 55 counts the number of dots in a certain range for each of the images for comparison and compares the numbers of dots at the same positions to calculates the matching degree.

Occlusion: A front and back relationship of objects in a three-dimensional image. The image comparison unit 55 compares between the images for comparison with respect to each of the objects formed in the image to determine whether the objects each of which has an area equal to or larger than a certain area are formed in the same shape to calculate the matching degree.

Target or background: The ratio between the background and the other portion. The image comparison unit 55 divides each of the two images for comparison into a background and the other portion and compares between the two images with respect to a planner dimension to calculate the matching degree.

MTF (bokeh): Spatial frequency. The image comparison unit 55 calculates the MTF for each of the two images and compares between the two images with respect to the MTF to calculate the matching degree.

S/N (noise): Corresponding to the sharpness of an image (log (maximum value/variance of shades)). The image comparison unit 55 calculates the S/N for each of the two images for comparison and compares between two images with respect to the S/N to calculate the matching degree.

In addition, as a method of calculating the matching degree, index or algorithm includes a sum of squared difference (SSD), a sum of absolute difference (SAD), a normalized cross correlation (NCC), a zero means normalized cross correlation (ZNCC), a mean squared error (MSE), a peak signal to noise ratio (PSNR), a structural similarity (SSIM), a histogram intersection, etc.

In addition, when the visual check result reception unit 56, which is described below in detail, receives a result obtained by visually-checking, indicating "MATCH" (the two comparison targets are the same with each other, or identical to each other), the image comparison unit 55 updates the matching degree of the image pair 7 to a value indicating "exactly match" (for example, 1.0). Hereinafter, the result obtained by visually-checking may be referred to as a visual check result. When the visual check result reception unit 56 receives the visual check result indicating "NOT MATCH" (the two comparison targets are not the same with each other, or are not identical to each other), the image comparison unit 55 updates the matching degree of the image pair 7 to a value indicating "NOT MATCH" (for example, a value in a range of 0.5 to 0.8).

The visual check result reception unit 56 receives the visual check result, which is obtained by a visual check performed by a user to determine whether the two images match each other (whether the two images are the same with each other, or identical to each other). That is, when the user actually sees (visually checks) the image pair 7, and the visual check result is different from the determination result of the information processing device 50, the user inputs "MATCH" or "NOT MATCH" to the terminal device 30. The visual check result reception unit 56 accepts the user input.

The image group pair matching information generation unit 57 generates a matching degree of the image group pair based on the plurality of matching degrees of the plurality of image pairs, which is included in the image group pair. That is, with respect to the image group pair 9, a matching degree is calculated, by taking each of the plurality of the matching degrees of the image pairs 7 into account. Namely, a degree of matching between the two image groups of the image group pair 9 is generated based on the plurality of matching degrees of the image pairs 7. Examples of a method of calculating a matching degree of the image group pair include an arithmetic mean, a geometric mean, a weighted mean, a harmonic mean, a trimmed mean, a sample variance, and an unbiased variance.

The image group pair matching information generation unit 57 binarizes the matching degree of the image group pair using a threshold value to generate information used for determining whether the two image groups of the image group pair 9 "MATCH" or do "NOT MATCH", namely whether the two image groups of the image group pair 9 are the same or not the same.

The screen information generation unit 58 generates screen information indicating a screen displayed on the terminal device 30 as a web server. The screen information generation unit 58 displays an image pair, a matching degree of the image pair, a matching degree of an image group pair, and the like. In addition, the screen information generation unit 58 displays a screen for accepting the user input of the visual check result. In addition, the screen information generation unit 58 may include a function of accepting a user input of designating the image group pair 9 for which the matching degree is desired to be calculated.

In addition, the information processing device 50 includes a storage unit 60 implemented by at least one of the HD 504 and the RAM 503 illustrated in FIG. 3. The storage unit 60 stores an evaluation file, the image pairs 7, the image group pair 9, information on the matching degrees of the image pairs 7, and information on the matching degree of the image group pair 9, for example.

Terminal Device

The terminal device 30 includes a second communication unit 31, a display control unit 32, and an operation reception unit 33. Each of the above-mentioned units included in the terminal device 30 is a function that is implemented by or that is caused to function by operating any of the elements illustrated in FIG. 3 according to an instruction from the CPU 501 according to a program, which is for the terminal device 30, expanded from the HD 504 to the RAM 503. The program is a web browser in the present embodiment, for example.

The second communication unit 31 included in the terminal device 30 transmits and receives various information to and from the information processing device 50. For example, the second communication unit 31 requests various types of web pages by Hyper Text Transfer Protocol (HTTP) communications, and transmits, to the information processing device 50, various types of operation content for the web pages.

The display control unit 32 analyzes various types of screen information received from the information processing device 50 to displays a screen on the display 506. The display control unit 32 displays the image pair 7, the matching degree between the two images of the image pair 7, the matching degree between the two groups of the image group pair 9, and the like. The operation reception unit 33 receives various operations on the web page (screen) displayed on the terminal device 30.

Procedure of Operation or Process

Figure 5:
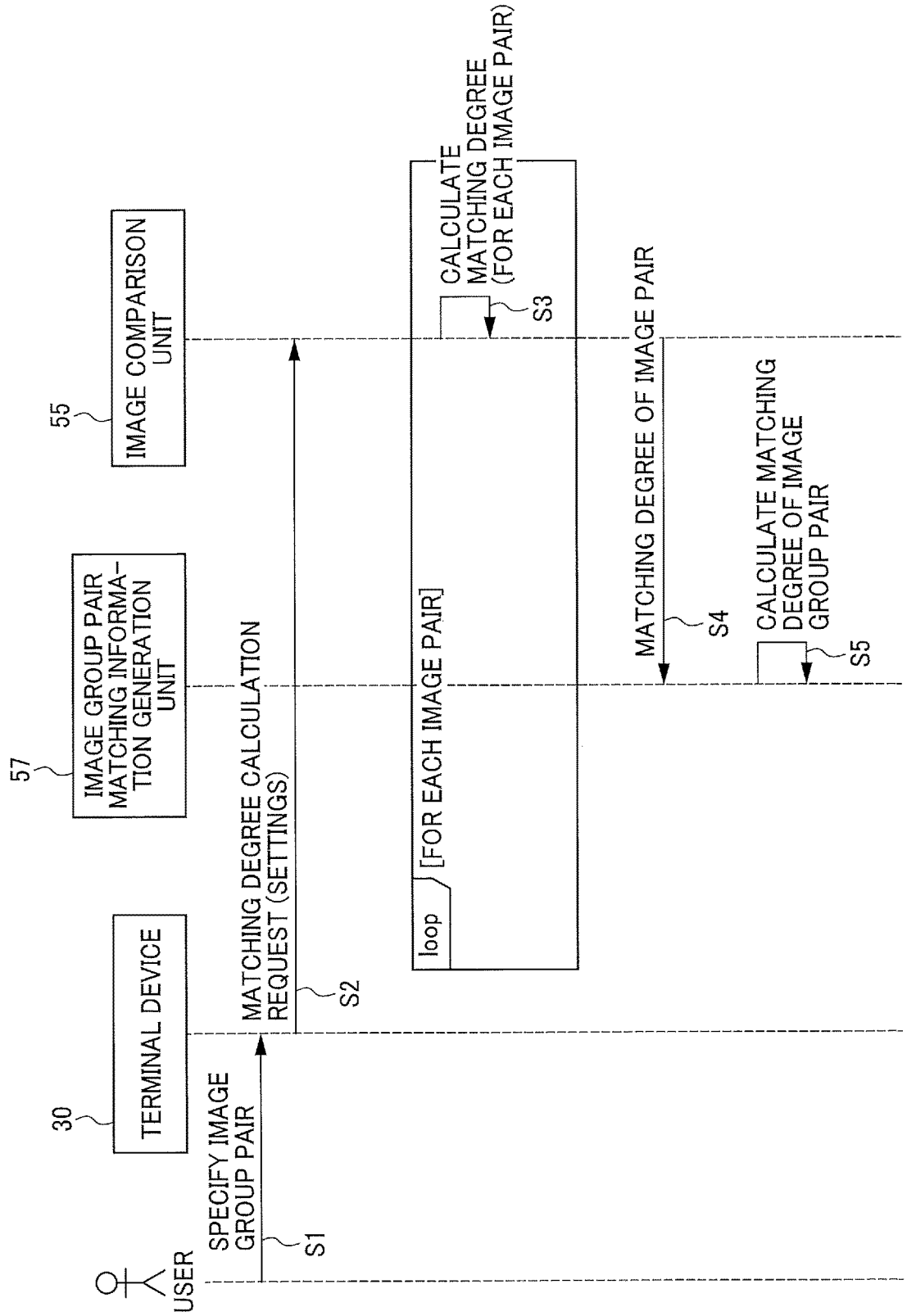
FIG. 5 is a sequence diagram illustrating an example of an overall procedure performed by an information processing system to calculate a matching degree of an image group pair, according to one or more embodiments.

FIG. 5 is a sequence diagram illustrating an example of an overall procedure performed by the information processing system 100 to calculate a matching degree of an image group pair, according to the present embodiment of the disclosure.

S1: A user operates the terminal device 30 so that the terminal device 30 communicates with the information processing device 50. Thereby, the screen information generation unit 58 of the information processing device 50 transmits to the terminal device 30 screen information of a user interface that receives settings for the matching determination for an image group pair. The second communication unit 31 of the terminal device 30 receives the screen information of the user interface, and the display control unit 32 causes the display 506 to display a screen based on the screen information. The user specifies a printer driver, a PDL module, and a plurality of evaluation files so that the information processing device 50 generates an image group. The operation reception unit 33 receives the above-described settings.

S2: The second communication unit 31 of the terminal device 30 specifies the plurality of evaluation files and the like, and transmits to the information processing device 50 a request that the information processing device 50 calculate a matching degree. Hereinafter, the request may be referred to as a matching degree calculation request.

S3: The first communication unit 59 of the information processing device 50 receives the matching degree calculation request, the specified plurality of evaluation files, and the like. Accordingly, the information processing device 50 generates images to be printed, by using each of the old system and the new system, thereby generating the image pairs 7 of which the number is the same as the number of evaluation files.

The control unit 51 activates the print application 52 corresponding to each evaluation file, and the print application 52 generates the print data of each specified evaluation file by the specified print conditions. Print data (*.prn, *.ps) is stored in the storage unit 60. When the evaluation file is in a format such as a prn file, a .ps file, or a portable document format (PDF) file that does not require the print application 52 to print out the file, the print data is not generated and the file is copied to the storage unit 60 as it is. In addition, when the evaluation file is an image file such as png or jpeg, the file is saved as it is in the storage unit 60, which is for print data.

Subsequently, the control unit 51 activates the printer simulator 54, and the printer simulator 54 performs drawing processing on the generated print data using the designated PDL module to generate an image to be printed. The generated image to be printed is stored in the storage unit 60 as an image to be printed (image for printing). The image to be printed is generated in a format such as png, Jpeg, or Tiff. The control unit 51 performs the same processing with each of the old system and the new system.

The image comparison unit 55 calculates the matching degree of each image pair 7, which corresponds to the old system and the new system, acquired from the storage unit 60. The method of calculating the matching degree between the images of an image pair is described later with reference to FIG. 6 to FIG. 11.

S4: The image comparison unit 55 transmits the matching degree of each image pair 7 to the image group pair matching information generation unit 57.

S5: The image group pair matching information generation unit 57 calculates the matching degree of the image group pair, after the matching degrees of all of the image pairs 7 are calculated. The method of calculating the matching degree of the image group pair is described later with reference to FIG. 12.

Method of Calculating Matching Degree of Image Pair

The method of calculating a matching degree between the images of an image pair includes a method of calculating an SSD, an SAD, an NCC, a ZNCC, an MSE, a PSNR, an SSIM, a Histogram Intersection, etc. Hereinafter the above-mentioned method is referred to as a first method. In addition, there is a method of determining whether the two comparison targets are identical to each other or not with the human visual perception. Hereinafter, this method is referred to as a second method. Accordingly, there are two main method to determine whether the two comparison targets are the same or not (to obtain the matching degree).

Figure 6:
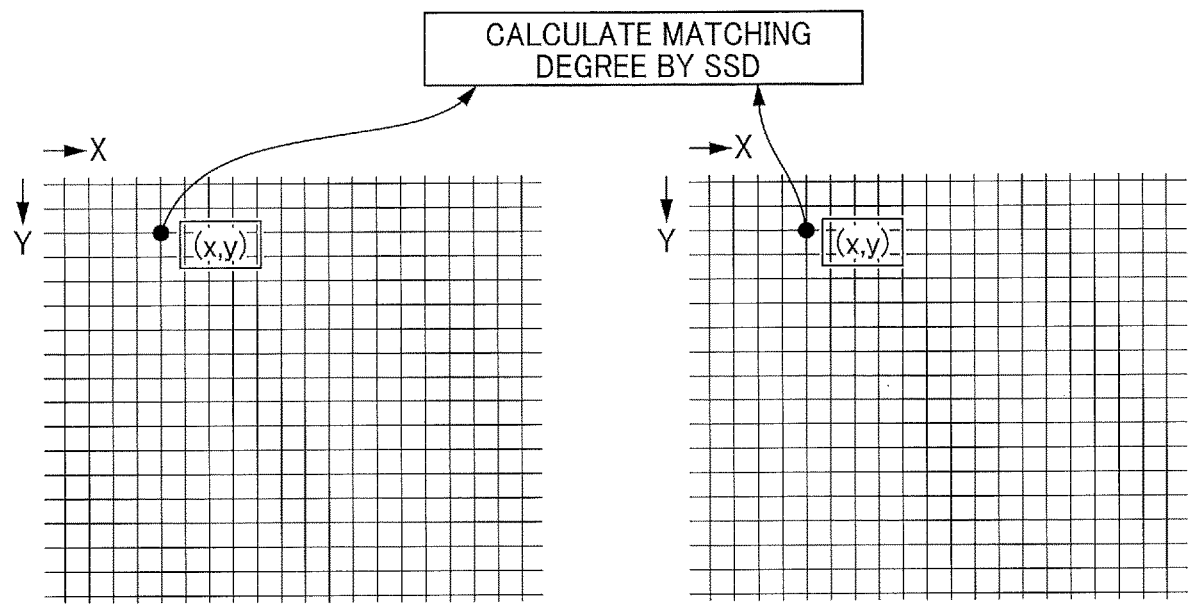
FIG. 6 is a diagram illustrating a method of calculating a matching degree of an image pair by an image comparison unit according one or more embodiments.

A description of an example of the first method is given below with reference to FIG. 6. FIG. 6 is a diagram illustrating a method of calculating a matching degree of an image pair by the image comparison unit 55 according to the present embodiment of the disclosure. In FIG. 6, a part of each of the two images to be compared is enlarged and displayed. The image comparison unit 55 compares the two images for each pixel position that is determined according to resolution of the image (for example, in a case of an image having the resolution of 1980×1280, the vertical is equally divided into 1980 and the horizontal is equally divided into 1280). In FIG. 6, intersection points of the mesh are the pixel positions.

When pixels in one of the two images and pixels in the other one of the two images have the same pixel values at the same pixel positions in each of the two images, a determination indicates that there is no difference between the images. On the other hand, when pixels for comparison do not have the same pixel values, a determination indicates that there is a difference between the images. As a method of digitizing the above-described difference, an SSD, an SAD, an NCC, a ZNCC, an MSE, a PSNR, or an SSIM may be used, for example. In addition, the Histogram Intersection may be used as a method of digitizing the difference in color. Since a formula used to obtain such a value is known, the detailed description is omitted.

In addition to or in alternative to simply comparing between the pixel values, comparison of the two images may be performed in the color, the shape, the layout, the hue, the saturation, the lightness, the luminance, the contrast, the color histogram, the edges, the corners, the character thickness, the font, the dither, the character-likeness, the illustration-likeness, the graphic-likeness, the photographic-likeness, the error diffusion, the occlusion, the target or background, the MTF (blurring), the S/N (noise), or the like, and a difference obtained by the comparison may be digitized.

A description of the second method is given below. Although a determination for each pixel obtained by the first method may seem to indicate a large difference, such an infinitesimal difference is difficult to be noticed with the human visual perception. Accordingly, a matching determination is performed on the basis of ambiguous matching. Thereby, a determination result that is close to the one obtained with the human visual perception may be obtained.

In the case of the ambiguous matching, when pixels, each of which is determined to be recognizable with the human visual perception, of a difference image of the two images are arranged in a manner that the pixels are recognizable with the human visual perception, it is regarded as a visible difference ("not match" (not the same)). Examples of an arrangement of difference that is recognizable with the human visual perception include the following.

(i) The pixels each of which is determined as a difference are continuously arranged to a size equal to or larger than a size that is recognizable with the human visual perception.

(ii) The pixels each of which is determined as a difference are arranged to occupy a ratio greater than a ratio that is recognizable with the human visual perception in a certain area.

(iii) The pixels each of which is determined as a difference are arranged in a specified arrangement pattern.

In the following, a method of recognizing each arrangement of difference is to be described.

A description is given below of (i): The pixels each of which is determined as a difference are continuously arranged to a size equal to or larger than a size that is recognizable with the human visual perception.

The image comparison unit 55 calculates a difference of pixel value between the two images of the image pair 7 for each pixel position to generate a difference image. Then, the image comparison unit 55 detects, from the difference image, a set of continuous differences, which are pixels (pixel positions) each of which is determined as a difference. Hereinafter, the set of continuous differences may be referred to as a continuous difference).

Figure 7A:
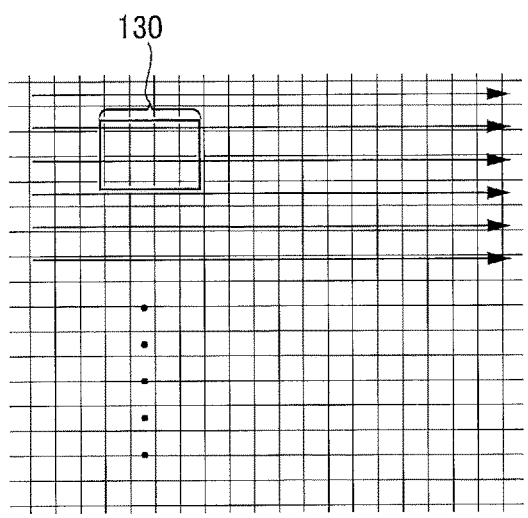
FIG. 7A and FIG. 7B are diagrams illustrating a method of detecting a continuous difference having a size that is equal to or bigger than a size recognizable with the human visual perception according to one or more embodiments.
Figure 7B:
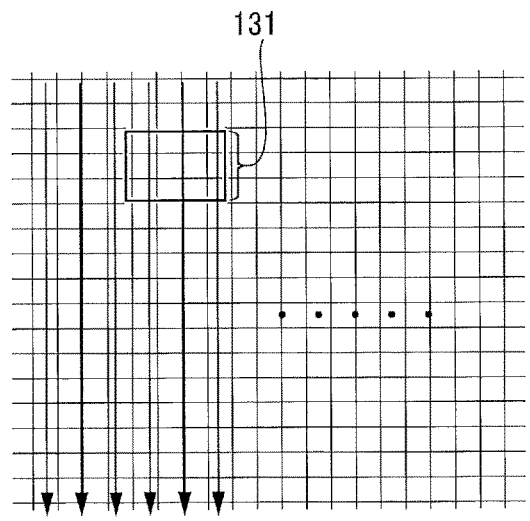

FIG. 7A and FIG. 7B are diagrams illustrating a method of detecting a continuous difference having a size that is equal to or larger than the size recognizable with the human visual perception, according to the present embodiment of the disclosure. In FIG. 7A, the pixel positions are scanned in the horizontal direction. Accordingly, when there is a difference equal to or larger than a size of difference 130, which is the size recognizable with the human visual perception, in the horizontal direction, the difference is detectable.

In FIG. 7B, the pixel positions are scanned in the vertical direction. Accordingly, when there is a difference equal to or larger than a size of difference 131, which is the size recognizable with the human visual perception, in the horizontal direction, the difference is detectable.

The arrangement of difference of a rectangular shape is detected by scanning in the vertical direction and in the horizontal direction, in FIG. 7A and FIG. 7B, respectively. The image comparison unit 55 detects a length of the continuous difference in each of the vertical direction and horizontal direction. In addition, scanning may be performed in a diagonal direction.

Then, the image comparison unit 55 compares the length of the continuous difference with a predetermined length (threshold value), and when the length of the continuous difference is longer than the predetermined length, the image comparison unit 55 records at the pixel positions of the continuous difference to indicate that the length is longer than the predetermined length. For example, a table capable of recording a "difference" for each pixel position is prepared, and the "difference" is recorded at all the pixel positions corresponding to the continuous difference that is longer than the predetermined length. When the length of the continuous difference is equal to or less than the threshold value, the image comparison unit 55 determines that the targets for comparison are the same with each other.

The image comparison unit 55 uses, for example, the "number of pixel positions recorded as "differences"/"a total number of pixels" as the matching degree.

A description is given below of (ii): The pixels each of which is determined as a difference are arranged to occupy a ratio greater than a ratio that is recognizable with the human visual perception in a certain area.

In this case, the image comparison unit 55 sequentially moves a window that encloses pixel positions in the difference image, and determines whether there is a set of differences, which are pixels (pixel positions) each of which is determined as a difference, occupying a ratio greater than the ratio that is recognizable with the human visual perception in the window or not. A size of the window corresponds to the certain area.

Figure 8:
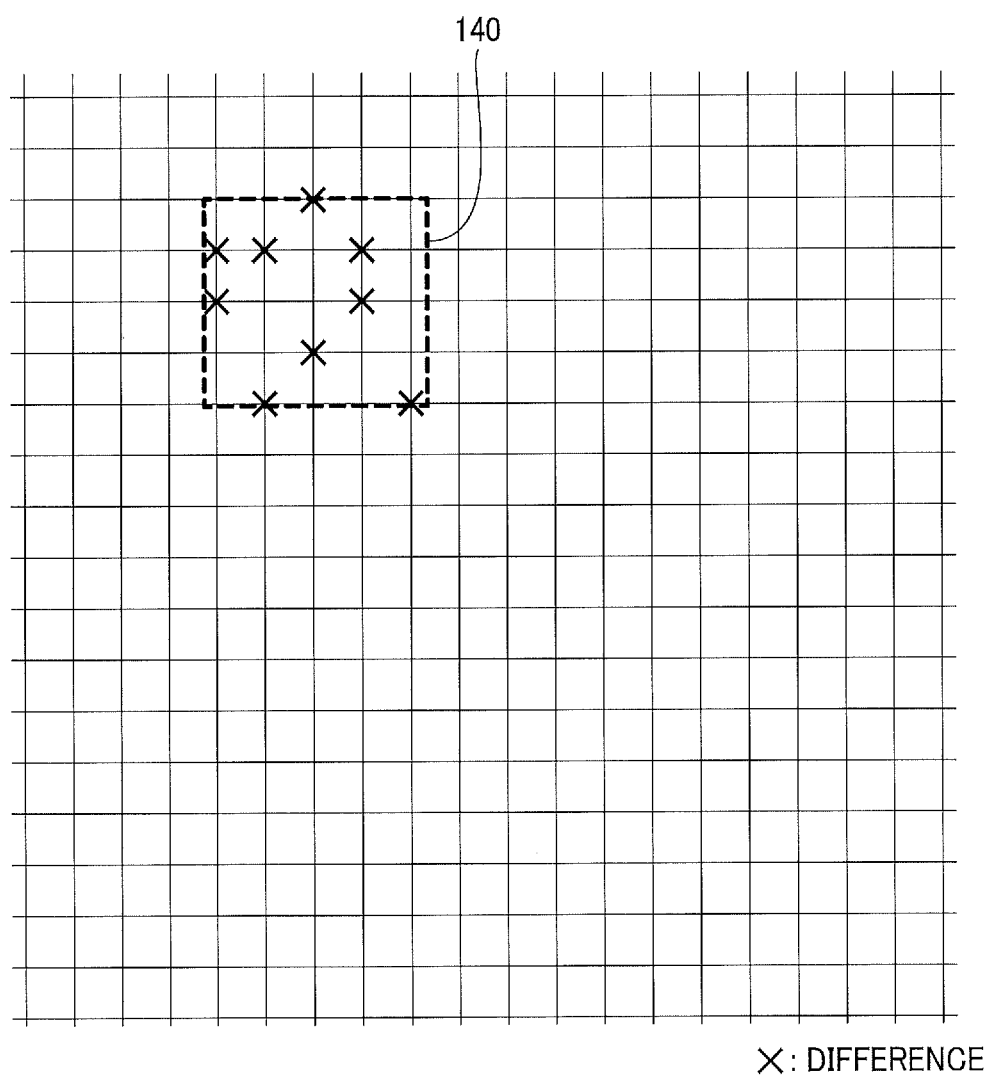
FIG. 8 is a diagram illustrating a method of detecting a set of differences that occupies, in a certain area, a ratio greater than a ratio that is recognizable with the human visual perception according to one or more embodiments.

FIG. 8 is a diagram illustrating a method of detecting the set of differences that occupies a ratio greater than the ratio, which is recognizable with the human visual perception, in the certain area, according to the present embodiment of the disclosure. In the example of FIG. 8, a window 140 having 4×4 pixels is illustrated, but the size of the window 140 is an example and not the limiting. The window 140 moves in a manner that a pixel position at the center of the window 140 starts from at a corner of the upper left and moves to the right end pixel by pixel, at the right end, the window 140 goes down by one pixel, and then returns to the left in the same manner, for example. Such the above-described movement is repeated until the pixel position at the center comes to the lower right corner.

The window 140 having 4×4 pixels includes 4×4=16 pixel positions. The image comparison unit 55 counts the number of pixel positions each of which is determined as a difference in the window. In FIG. 8, for the sake of explanatory convenience, nine pixel positions are illustrated as being determined as the differences.

The image comparison unit 55 determines whether a condition of "9/16>a predetermined ratio" is satisfied or not, and when the condition is satisfied, the image comparison unit 55 records, in a table that is capable of recording a "difference" for each pixel position, the "difference" for each of all the pixel positions corresponding to the nine pixels in the window. When the length of the continuous difference is equal to or less than the threshold value, the image comparison unit 55 determines that the targets for comparison are the same with each other.

The image comparison unit 55 uses, for example, the "number of pixel positions recorded as "differences"/"a total number of pixels" as the matching degree.

A description is given below of (iii): The pixels each of which is determined as a difference are arranged in a specified arrangement pattern.

In this case, the image comparison unit 55 holds (stores, records) a specified arrangement pattern. The image comparison unit 55 performs pattern matching on a difference image with an arrangement pattern and determines whether there is an arrangement of difference that matches the arrangement pattern.

Figure 9A:
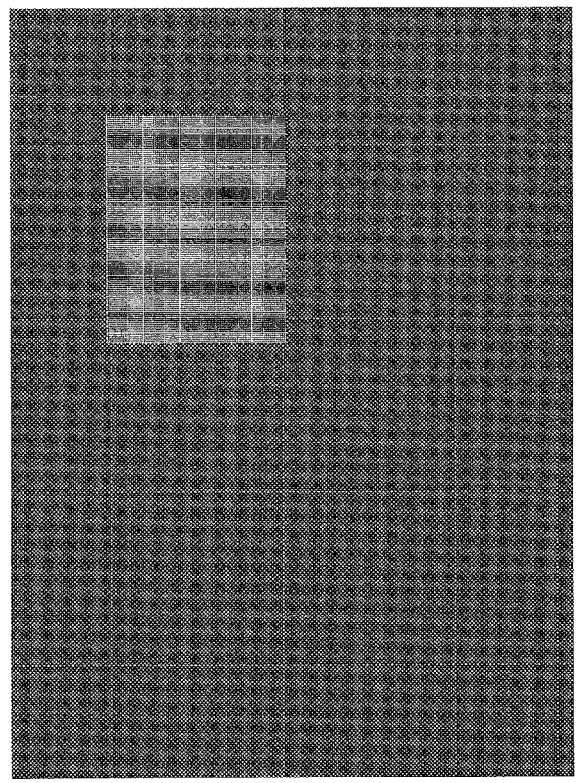
FIG. 9A and FIG. 9B are diagrams illustrating a method of generating a difference image, according to one or more embodiments.
Figure 9B:
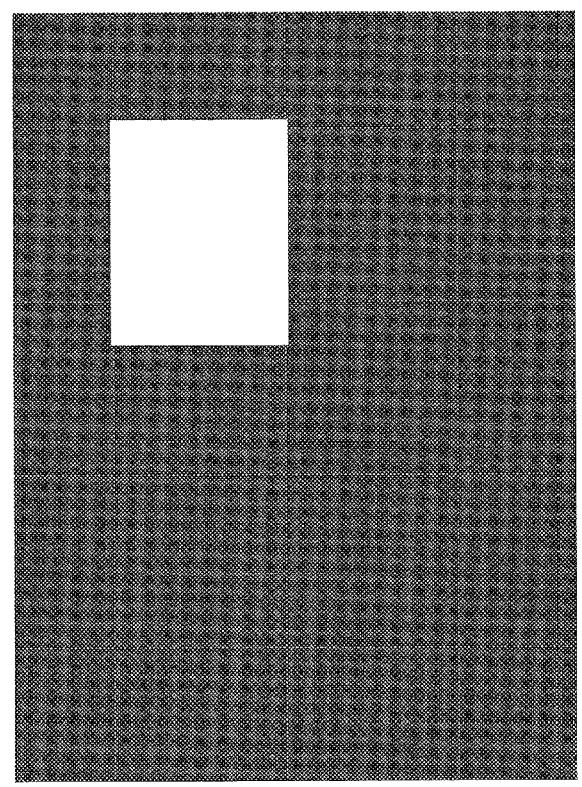

FIG. 9A and FIG. 9B are diagrams illustrating a method of generating a difference image, according to the present embodiment of the disclosure. FIG. 9A is a diagram illustrating an example of a first image for comparison (may be referred to as a comparison source), and FIG. 9B is a diagram illustrating an example of a second image for comparison (may be referred to as a comparison target). In FIG. 9A and FIG. 9B, the comparison source and the comparison target illustrated are clearly different from each other, for the sake of explanatory convenience, however, there is a case where the difference between the comparison source and the comparison target is not easily visually recognizable by a user.

Figure 10A:
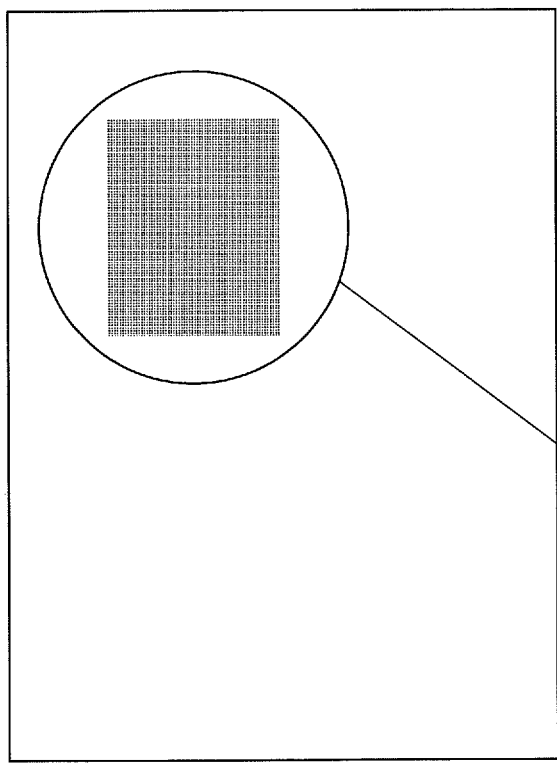
FIG. 10A, FIG. 10B, and FIG. 10C are diagrams illustrating an example of a difference image of two images, an example of an enlarged view of the difference image, and an example of an arrangement pattern, respectively, according to one or more embodiments.
Figure 10B:
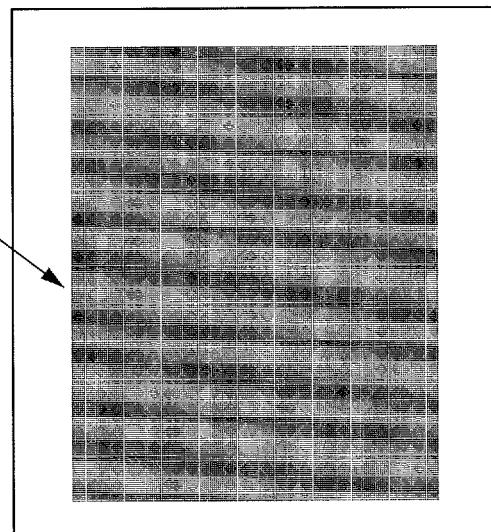
Figure 10C:
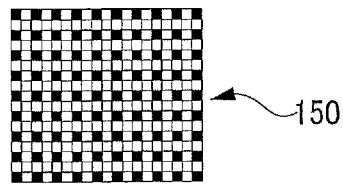

FIG. 10A is a diagram illustrating a difference image of the two images each of which is illustrated in one of FIG. 9A and FIG. 9B, according to the present embodiment of the disclosure. FIG. 10B is a diagram illustrating an enlarged view of the difference image, according to the present embodiment of the disclosure. Further, FIG. 10C is a diagram illustrating an arrangement pattern 150, according to the present embodiment of the disclosure. The arrangement pattern 150 is generated in advance as a difference pattern that is easily perceived by the human eye. The arrangement pattern 150 illustrated in FIG. 10C is an example, and may be a band shape, a circular shape, or a geometrical pattern, for example.

In a case where the difference illustrated as the enlarged view of FIG. 10B matches the arrangement pattern 150, when the image comparison unit 55 determines that there is a difference, the two images that have a difference perceived by human are detectable.

Figure 11:
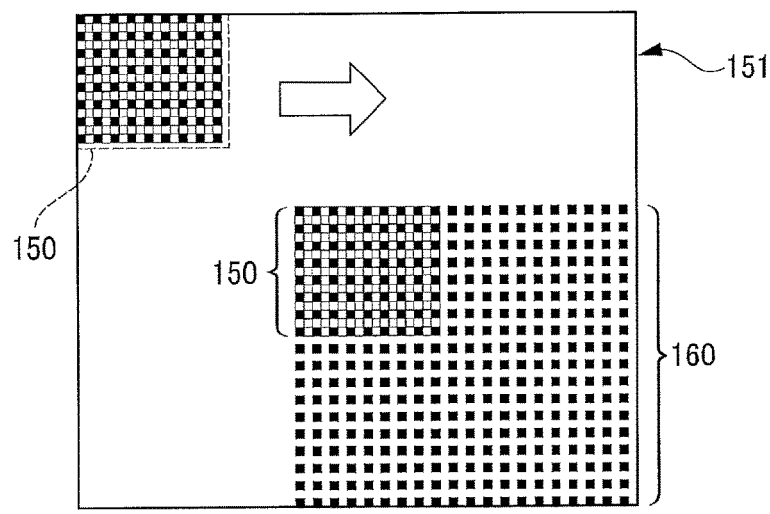
FIG. 11 is a diagram illustrating a method of detecting an arrangement pattern from an arrangement of difference, according to one or more embodiments.

FIG. 11 is a diagram illustrating a method of detecting an arrangement pattern from an arrangement of difference 160. In FIG. 11, for the sake of explanatory convenience, the arrangement of difference 160 has the same pattern as the arrangement pattern 150. The image comparison unit 55 moves the arrangement pattern 150 starting from at a corner of the upper left in the difference image 151 and moves to the right end pixel by pixel, at the right end, moves the arrangement pattern 150 down by one pixel, and then returns to the left in the same manner, for example. Such the above-described movement is repeated until the arrangement pattern 150 reaches the lower right corner.

The image comparison unit 55 determines whether a "difference" is recorded with respect to the difference image at the same position as each of the pixels of the arrangement pattern 150, and when the "difference" is recorded at each position of all the pixels, the arrangement pattern 150 is determined as being detected from the difference image 151. Alternatively, when a "difference" is recorded at each position of a certain number or more (a certain percentage or more) of the pixels, the arrangement pattern 150 is determined as being detected from the difference image 151.

In FIG. 11, there is the arrangement of difference 160 that matches the arrangement pattern 150 at the lower right of the difference image 151, and the arrangement of difference 160 is detectable by the image comparison unit 55. The image comparison unit 55 records, in a table that is capable of recording a "difference" for each pixel position, the "difference" for each of the corresponding pixel positions that matches the arrangement pattern 150.

The image comparison unit 55 uses, for example, the "number of pixel positions recorded as "differences"/"a total number of pixels" as the matching degree.

Calculation of Matching Degree Between Groups of Image Group Pair

A description is given of a method of calculating a matching degree between groups of an image group pair. After the matching degrees between the two images for all of the plurality of image pairs 7 are calculated, the image group pair matching information generation unit 57 calculates a matching degree between the two image groups of the image group pair.

The image group pair matching information generation unit 57 calculates the matching degree of the image group pair by using an arithmetic mean, a geometric mean, a weighted mean, a harmonic mean, a trimmed mean, a sample variance, an unbiased variance, or the like.

Arithmetic mean: The so-called arithmetic average. When the matching degree of the image pair 7 is $a_i$ (i is a number of the image pair 7), the arithmetic mean is $\Sigma a_i/N$. N is the number of the image pairs 7.

Geometric mean: The square root $\sqrt{}$ ($\Pi a_i$) of a value obtained by multiplying the matching degrees $a_i$ of the image pairs 7.

Weighted mean: Rather than simply averaging the values, averaging by adding a weight of value (=weight value). If the weight is $p_i$, the weighted mean is $\Sigma p_i a_i/N$. The $p_i$ may be specified by a user when the user selects an evaluation file or may be assigned by an information processing system according to a file type (extension).

Harmonic mean: $N/(\Sigma(1/a_i))$.

Trimmed mean: An arithmetic mean calculated by excluding data close to the minimum value and data close to the maximum value.

Sample variance: $(1/N)\Sigma (a_i\text{-arithmetic mean})^2$.

Unbiased variance: $n/(n-1)\times$sample variance.

Example of Calculation of Matching Degree Between Groups of Image Group Pair

Figure 12:
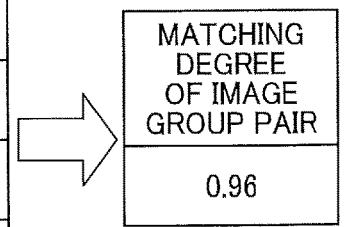
FIG. 12 is a diagram illustrating an example of data indicating matching degrees of image pairs and a matching degree of an image group pair, according to one or more embodiments.

FIG. 12 is a diagram illustrating an example of data representing the matching degrees of the image pairs 7 and the matching degree of the image group pair (there are an image group A and an image group B), according to the present embodiment of the disclosure.

In FIG. 12, each of the image group A and the image group B has five images, and the matching degree is calculated for each of the five image pairs 7. When the matching degree of the image group pair is to be obtained by the arithmetic mean, the following applies.

Matching Degree of Image Group Pair=(0.96+1.0+ 0.97+0.93+0.94)/5=0.96

For example, in a case where the threshold value is 0.95, the image group pair matching information generation unit 57 is to determine that the two image groups of an image group pair are the same when a value of the matching degree is equal to or greater than 0.95. In the above-described case, the image group pair matching information generation unit 57 determines that the two image groups of the image group pair 9, which is illustrated in FIG. 12, are the same, namely one of the two image groups matches the other one of the two image groups in the image group pair 9.

Update of Matching Degree According to Visual Check

A description is given below of updating a matching degree of an image pair and updating a matching degree of an image group pair according to a determination result obtained by a visual check performed on the image pairs 7 by a user, with reference to FIG. 13 to FIG. 17.

Figure 13:
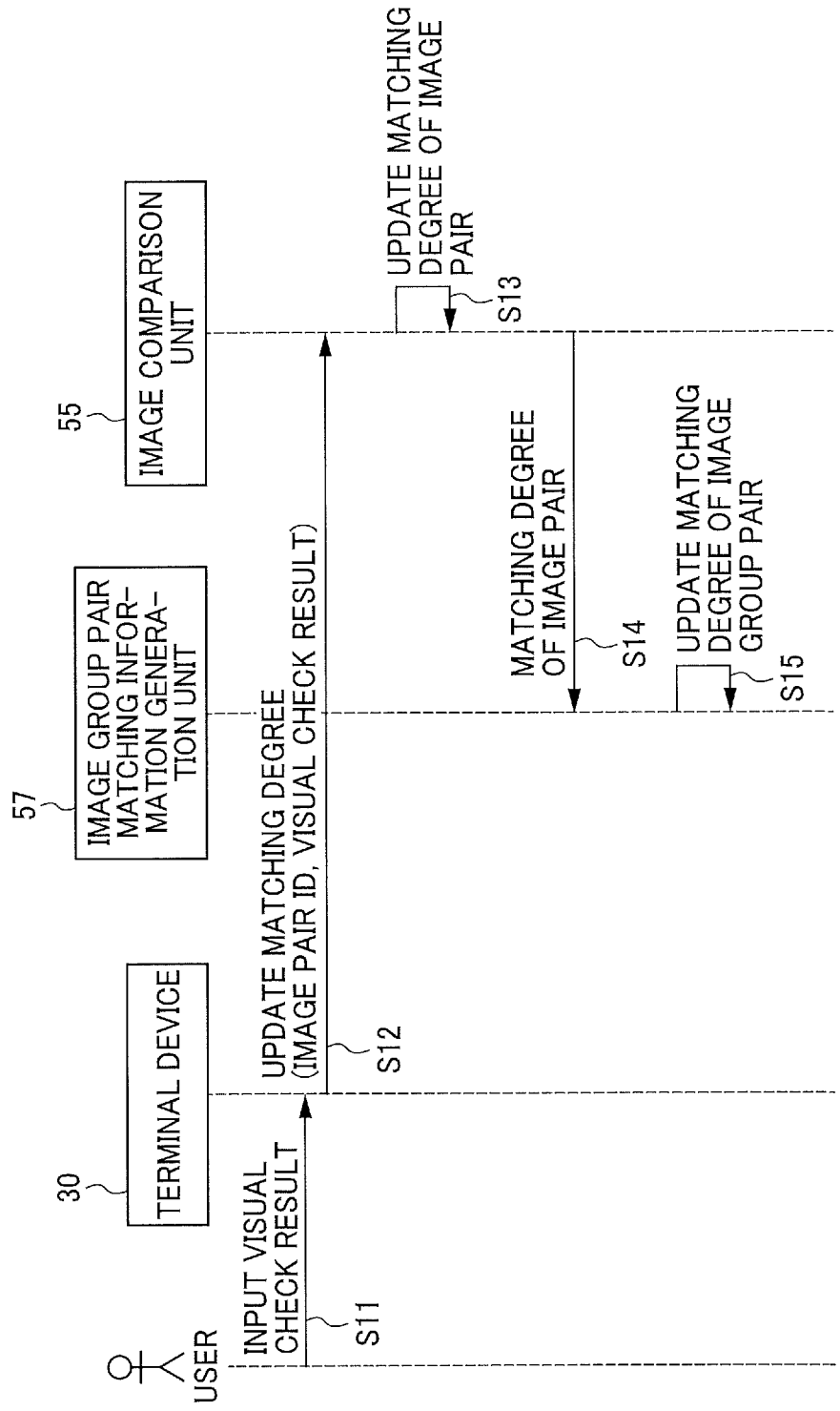
FIG. 13 is a sequence diagram illustrating an example of a flow of updating a matching degree of an image pair and a matching degree of an image group pair in a case where a user input a visual check result, according to one or more embodiments.

FIG. 13 is a sequence diagram illustrating an example of a flow of updating a matching degree of an image pair and a matching degree of an image group pair in a case where a user input a visual check result, according to the present embodiment of the disclosure.

S11: The information processing device 50 transmits all the generated image pairs 7 to the terminal device 30. The terminal device 30 displays the image pairs 7, the user inputs a visual check result (MATCH or NOT MATCH) for each image pair 7. If the determination result of the information processing device 50 and the determination result of the user (visual check result) are the same, the input may not be performed. The operation reception unit 33 of the terminal device 30 receives the input. A description of an example of the input is given later with reference to FIG. 15 and FIG. 16.

S12: The second communication unit 31 of the terminal device 30 specifies a corresponding image pair ID and transmits the visual check result and the image pair ID to the information processing device 50.

S13: The first communication unit 59 of the information processing device 50 receives the image pair ID and the visual check result, and the image comparison unit 55 updates, with the visual check result, the matching degree of the image pair 7 that is identified by the image pair ID. When the visual check result is "MATCH", namely in response to the visual check result indicating "MATCH", the image comparison unit 55 updates the matching degree of the image pair 7 to a value indicating "exactly match" (for example, 1.0). When the visual check result is "NOT MATCH", namely in response to the visual check result indicating "NOT MATCH", the image comparison unit 55 updates the matching degree of the image pair 7 to a value indicating "not match" (for example, a value in a range of 0.5 to 0.8).

S14: The updated matching degree of the image pair 7 is input to the image group pair matching information generation unit 57.

S15: Since the matching degree of the image pair 7 has been updated, the overall matching degree also changes. Accordingly, the image group pair matching information generation unit 57 updates the matching degree of the image group pair. The detailed description of the above-described update is given later, with reference to FIG. 17.

Figure 14:
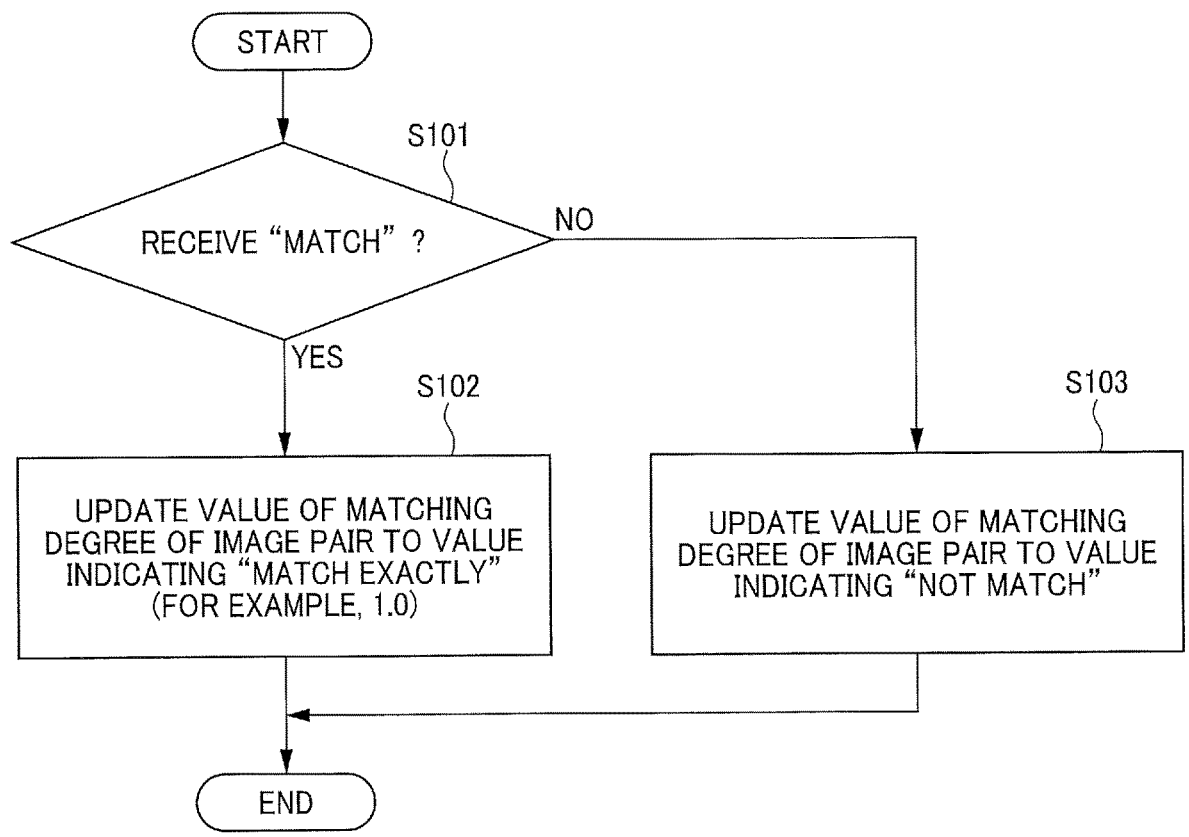
FIG. 14 is a flowchart illustrating an example of updating a matching degree of an image pair, which is performed by an image group pair matching information generation unit according to one or more embodiments.

FIG. 14 is a flowchart illustrating an example of updating the matching degree of the image pair, which is performed by the image group pair matching information generation unit 57, according to the present embodiment of the disclosure.

The image group pair matching information generation unit 57 determines whether the first communication unit 59 receives "MATCH" or not (S101).

When receiving "MATCH", the image group pair matching information generation unit 57 updates the matching degree to a value indicating "exactly match" (for example, 1.0) (S102).

When receiving "NOT MATCH", the image group pair matching information generation unit 57 updates the matching degree to a value indicating "not match" (S103).

Visual Check Screen

Figure 15:
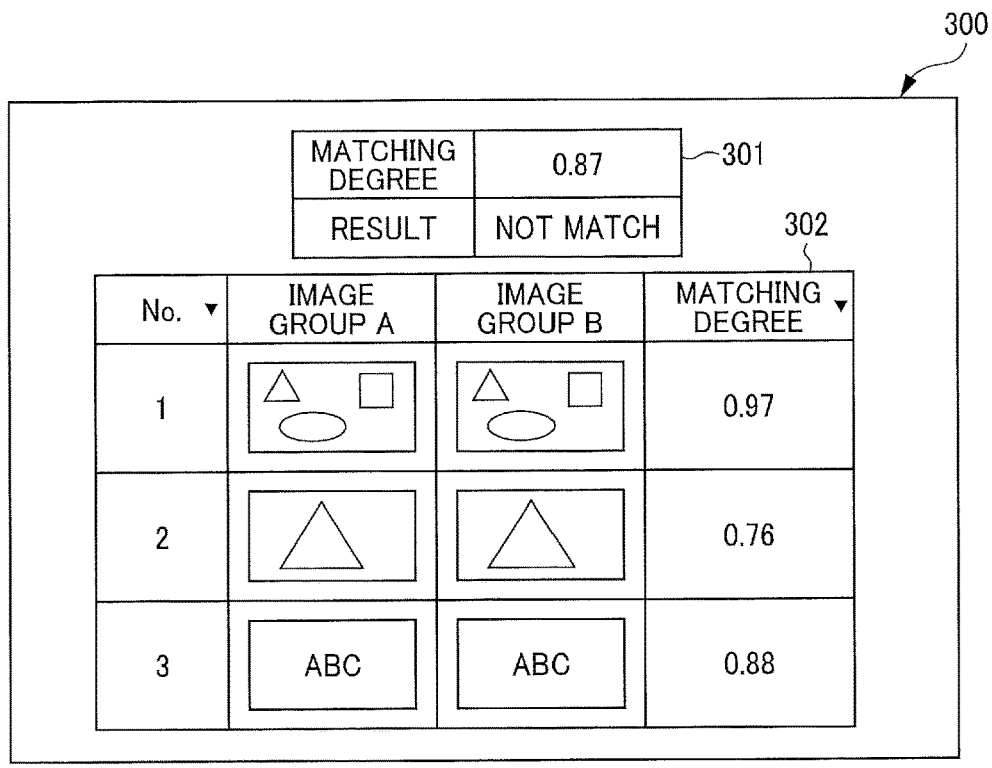
FIG. 15 is a diagram illustrating an example of a list screen displaying a list of image pairs displayed by a terminal device according to one or more embodiments.

FIG. 15 is a diagram illustrating an example of a list screen 300 displaying a list of the image pairs 7 displayed by the terminal device 30 according to the present embodiment of the disclosure. The list screen 300 has a determination result section 301 and an image section 302. In the determination result section 301, the matching degree of the image group pair, and the determination result are displayed. In the image section 302, each image of the image group A, each image of the image group B, and the matching degree of each image pair 7 are displayed.

The list screen 300 allows the user to check each image pair 7, each matching degree of the image pair, the matching degree of the image group pair, and whether the two groups of the image group pair 9 matches. The terminal device 30 may sort, by the matching degree, the image pairs 7 to be displayed.

When the threshold value of the matching degree of the image group pair is 0.95, in the example of FIG. 15, the image group pair 9 of which a value of the matching degree of the image group pair is 0.87, is determined as "NOT MATCH".

The user may enlarge each image pair 7 to be displayed and visually check whether each image pair 7 is the same with each other or not.

Figure 16:
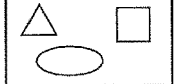
FIG. 16 is a diagram illustrating an example of a visual check result input screen on which one of image pairs is enlarged to be displayed, according to one or more embodiments.

FIG. 16 is a diagram illustrating an example of a visual check result input screen 310 on which one of the image pairs 7 (for example, Image Pair No. 2) is enlarged to be displayed, according to the present embodiment of the disclosure. The visual check result input screen 310 includes an image pair section 311, a check result input field 312, and an update button 313. The user may input, in the check result input field 312, the visual check result (whether the images of the pair are the same each other or not) for the image pair 7 displayed in the image pair section 311.

When the user presses the update button 313, the visual check result is transmitted to the information processing device 50. The image comparison unit 55 of the information processing device 50 updates the matching degree of the image pair, and the image group pair matching information generation unit 57 updates the matching degree of the image group pair. The visual check result input screen 310 illustrated in FIG. 16 transitions to the list screen 320 illustrated in FIG. 17.

FIG. 17 is a diagram illustrating an example of a list screen 320 when the user inputs "MATCH" with respect to the one of the image pair 7 (for example, Image Pair No. 2) on the visual check result input screen 310 illustrated in FIG. 16, according to the present embodiment of the disclosure. Comparing FIG. 17 and FIG. 15, the matching degree of the one of the image pairs 7 (Image Pair No. 2) is updated to 1.0 in FIG. 17. That is, when the visual check result input by the user (user input operation) is "MATCH", the image comparison unit 55 updates the matching degree of the corresponding image pair 7 to "1.0" (a value indicating "exactly match", for example). The updated value is not limited to "1.0", but at least the value is to be updated to a value higher than the original value of the matching degree.

Since the one of the matching degrees of the image pairs 7 has been updated, the image group pair matching information generation unit 57 updates the matching degree of the image group pair. In the case of the arithmetic mean, the image group pair matching information generation unit 57 performs the update based on the following equation.

Matching Degree of Image Group Pair=(0.97+1.0+ 0.88)/3=0.95

Accordingly, the matching degree of the image group pair is equal to or greater than the threshold value, and the image group pair matching information generation unit 57 determines that the two image groups of the image group pair 9 "MATCH" (are the same with each other) as illustrated in the determination result section 301 of FIG. 17.

As described above, according to the update of the matching degree of the image pair 7 performed by the information processing device 50 based on the visual check result input by the user (user input operation), the matching degree of the image group pair is also updated. As a result, the information on the sameness, which indicates whether the two image groups of the image group pair 9 "match" or do "not match" may be also changed.

Display Example of Matching Degree Based on Certain Features

A description is given below of a display example of the matching degree based on one or more certain features (image features) with reference to FIG. 18. FIG. 18 is a diagram illustrating an example of a list screen 330 displaying a list of the image pairs 7 displayed by the terminal device 30 based on features of color and shape, according to the present embodiment of the disclosure. In a determination result section 301 of FIG. 18, a matching degree 331 of the image group pair obtained based on color, a matching degree 332 of the image group pair obtained based on shape, and an average value 333 of the matching degrees (331, 332) are displayed. A determination result 334 is obtained by determining whether the average value 333 is equal to or greater than the threshold value.

Further, an image section 302 of FIG. 18 includes columns of a matching degree of the image group pair based on color 335 and a matching degree of the image group pair based on shape 336.

As described above, the image group pair matching information generation unit 57 is capable of calculating a matching degree of each image pair 7 by focusing on one or more certain features, and the image group pair matching information generation unit 57 is capable of calculating a matching degree of the image group pair for each feature. That is, the image group pair matching information generation unit 57 may determine whether the two image groups of the image group pair match or not based on, for example, an average of the matching degrees of the features. The image group pair matching information generation unit 57 may determine whether the two image groups of the image group pair match or not for each feature without obtaining the average of the matching degrees of the features.

As described above, the information processing system 100 according to the present embodiment of the disclosure calculates the matching degree of the image group pair 9 based on the plurality of matching degrees of the plurality of image pairs 7, thereby determining whether the two image groups 8 are identical to each other (match) or not, as a whole, based on a comparison result obtained from a large number of image pairs, which are the image pairs 7.

In a conventional technique, information on sameness between two image groups of an image group pair is not generated. The image group pair is a pair of two image groups. Each image group of the two image groups is generated by a different system.

According to one or more embodiments of the present disclosure, an information processing device capable of generating information on sameness between two image groups of an image group pair is provided.

Variation

The above-described embodiment is illustrative and do not limit the present invention. Thus, numerous additional modifications and variations are possible in light of the above teachings within the scope of the present invention. Any one of the above-described operations may be performed in various other ways, for example, in an order different from the one described above.

For example, the functional configuration illustrated in FIG. 4 is divided according to main functions in order to facilitate understanding of processing performed by the information processing device 50. Each processing unit or each specific name of the processing unit is not to limit a scope of the present disclosure. The processing of the information processing device 50 may be divided into more pieces of processing according to the processing details. In addition, such division can be such that a single processing unit includes a plurality of processes.

Further, the printer simulator may be included in a server device that communicates with the information processing device 50, in addition to being included in the information processing device 50.

The apparatuses or devices described in each embodiment are merely one example of plural computing environments that implement one or more embodiments disclosed herein. In some embodiments, information processing device 50 includes multiple computing devices, such as a server cluster. The multiple computing devices are configured to communicate with one another through any type of communication link including a network, shared memory, etc., and perform the processes described in this disclosure. Similarly, terminal device 30 may include such multiple computing devices configured to communicate with one another.

Each of the functions of the described embodiments may be implemented by one or more processing circuits or circuitry. Here, the "processing circuit or circuitry" in the present disclosure includes a programmed processor to execute each function by software, such as a processor implemented by an electronic circuit, and devices, such as an application specific integrated circuit (ASIC), a digital signal processors (DSP), a field programmable gate array (FPGA), and conventional circuit modules arranged to perform the recited functions.

Any one of the above-described operations may be performed in various other ways, for example, in an order different from the one described above.

Although the embodiments of the disclosure have been described and illustrated above, such description is not intended to limit the disclosure to the illustrated embodiments. Numerous additional modifications and variations are possible in light of the above teachings. It is therefore to be understood that within the scope of the appended claims, the embodiments may be practiced otherwise than as specifically described herein. For example, elements and/or features of different illustrative embodiments may be combined with each other and/or substituted for each other within the scope of this disclosure and appended claims.

What is claimed is:

1. An information processing device for checking whether there is no failure or problem in an image output function of an image output system, the device, comprising circuitry configured to output a plurality of image pairs, each of which is an image pair composed of a first image and a second image, by performing:

inputting test data into a first image output system to output the first image, the first image output system having no failure or problem in an image output function thereof, and inputting the test data into a checking target system to output the second image, calculate a matching degree for each image pair in the plurality of image pairs by performing:

calculating, for all pixels that make up for each of two images of the image pair, pixel values of the two images, one image of the image pair belonging to a first group of a plurality of first images and the other image of the image pair belonging to a second group of a plurality of second images, and calculating, for all pixels that make up for each of the two images, the matching degree between the two images based on the calculated pixel values at same pixel positions in each of the two images, and calculating, based on a plurality of matching degrees, a sameness value indicative of sameness between the first group and the second group, the plurality of matching degrees being obtained by the calculating the matching degree for each image pair in the plurality of image pairs, the sameness value including one of an arithmetic mean, a geometric mean, a weighted mean, a harmonic mean, a trimmed mean, a sample variance, and an unbiased variance, and generate information on whether there is no failure or problem in an image output function of the checking target system based on a comparison of the calculated sameness value with a threshold value.

2. The information processing device according to claim 1, wherein the circuitry generates information indicating whether the first group and the second group matches based on whether the sameness value is equal to or greater than the threshold value.

3. The information processing device according to claim 1, wherein the circuitry transmits the plurality of image pairs to a terminal device that communicates with the information processing device through a network, receives a visual check result by a user input operation, the visual check result indicating whether two images of the image pair match or not, updates, in response to the visual check result indicating that the two images of the image pair match, a value of the matching degree of the image pair, the updated value indicating that the two images of the image pair match exactly, and updates the sameness value according to the update of the matching degree of the image pair.

4. The information processing device according to claim 1, wherein the circuitry transmits the plurality of image pairs to a terminal device that communicates with the information processing device through a network, receives a visual check result by a user input operation, the visual check result indicating whether two images of the image pair match or not, updates, in response to the visual check result indicating that the two images of the image pair do not match, a value of the matching degree of the image pair, the updated value indicating that the two images of the image pair do not match, and updates the sameness value according to the update of the matching degree of the image pair.

5. The information processing device according to claim 1,
wherein the circuitry
focuses on a plurality of image features to calculate the plurality of matching degrees of the plurality of image pairs, and
calculates the sameness value based on the plurality of matching degrees of the plurality of image pairs, which are calculated based on the plurality of image features.

6. An information processing system, comprising:
the information processing device according to claim 1; and
a terminal device including terminal device circuitry configured to
receive, from the circuitry of the information processing device, the information on the sameness between the first group and the second group, and
display, on a display, the information on whether there is no failure or problem in an image output function of the checking target system.

7. A method of generating information for checking whether there is no failure or problem in an image output function of an image output system, the method, comprising:
outputting a plurality of image pairs, each of which is an image pair composed of a first image and a second image, by performing:
inputting test data into a first image output system to output the first image, the first image output system having no failure or problem in an image output function thereof, and
inputting the test data into a checking target system to output the second image,
calculating a matching degree for each image pair in the plurality of image pairs by performing:
calculating, for all pixels that make up for each of two images of the image pair, pixel values of the two images, one image of the image pair belonging to a first group of a plurality of first images and the other image of the image pair belonging to a second group of a plurality of second images, and
calculating, for all pixels that make up for each of the two images, the matching degree between the two images based on the calculated pixel values at same pixel positions in each of the two images, and
calculating, based on a plurality of matching degrees, a sameness value indicative of sameness between the first group and the second group, the plurality of matching degrees being obtained by the calculating the matching degree for each image pair in the plurality of image pairs, the sameness value including one of an arithmetic mean, a geometric mean, a weighted mean, a harmonic mean, a trimmed mean, a sample variance, and an unbiased variance, and
generating information on whether there is no failure or problem in an image output function of the checking target system based on a comparison of the calculated sameness value with a threshold value.

8. A non-transitory recording medium storing a plurality of instructions which,
when executed by one or more processors, cause the processors to perform a method for checking whether there is no failure or problem in an image output function of an image output system, the method, comprising:
outputting a plurality of image pairs, each of which is an image pair composed of a first image and a second image, by performing:
inputting test data into a first image output system to output the first image, the first image output system having no failure or problem in an image output function thereof, and
inputting the test data into a checking target system to output the second image,
calculating a matching degree for each image pair in the plurality of image pairs by performing:
calculating, for all pixels that make up for each of two images of the image pair, pixel values of the two images, one image of the image pair belonging to a first group of a plurality of first images and the other image of the image pair belonging to a second group of a plurality of second images, and
calculating, for all pixels that make up for each of the two images, the matching degree between the two images based on the calculated pixel values at same pixel positions in each of the two images, and
calculating, based on a plurality of matching degrees, a sameness value indicative of sameness between the first group and the second group, the plurality of matching degrees being obtained by the calculating the matching degree for each image pair in the plurality of image pairs, the sameness value including one of an arithmetic mean, a geometric mean, a weighted mean, a harmonic mean, a trimmed mean, a sample variance, and an unbiased variance, and
generating information on whether there is no failure or problem in an image output function of the checking target system based on a comparison of the calculated sameness value with a threshold value.

* * * * *